United States Patent [19]
Mumme et al.

[11] Patent Number: 5,364,402
[45] Date of Patent: Nov. 15, 1994

[54] TIBIAL SPACER SAW GUIDE

[75] Inventors: Charles W. Mumme; John D. Vinciguerra, both of Austin, Tex.

[73] Assignee: Intermedics Orthopedics, Inc., Austin, Tex.

[21] Appl. No.: 99,157

[22] Filed: Jul. 29, 1993

[51] Int. Cl.$^5$ .............................................. A61B 17/00
[52] U.S. Cl. ......................................... 606/88; 606/96
[58] Field of Search ..................... 606/86, 87, 88, 89, 606/96

[56] References Cited

U.S. PATENT DOCUMENTS

| | | | |
|---|---|---|---|
| 4,892,093 | 1/1990 | Zarnowski et al. | 606/88 |
| 4,963,152 | 10/1990 | Hofmann et al. | 623/18 |
| 5,122,144 | 6/1992 | Bert et al. | 606/88 |

*Primary Examiner*—Tamara L. Graysay
*Attorney, Agent, or Firm*—Richard L. Robinson

[57] ABSTRACT

A tibial spacer saw guide for guiding the resection of a bony defect of the lateral or medial condyle of the proximal tibia to accommodate a spacer to be implanted beneath a tibial baseplate of a tibial prosthesis. The saw guide includes a plate having a plurality of locating holes corresponding in spacing and location to pins extending from the inferior surface of the tibial baseplate. The plate has medial and lateral guide edges for guiding a sagittal osteotomy where the guide edges are located relative to the locating holes, and thus relative to the pegs of the tibial baseplate. The saw guide also includes an anterior block extending from the plate and having a plurality of slots for guiding a horizontal osteotomy for the spacer of selected depth. The plate rests on an initially resected surface, and thus the horizontal osteotomy for the spacer is located relative to the initial osteotomy surface. The block is repositionable relative to the plate such that the saw guide can be used for both medial and lateral spacers of both the left and right tibias.

12 Claims, 3 Drawing Sheets

TIBIAL SPACER SAW GUIDE

BACKGROUND OF THE INVENTION

1. Field of the Invention

The present invention relates generally to surgical instruments used during implantation of orthopedic joint replacement prostheses, and relates more particularly to a saw guide for guiding the resection of bony defects of the proximal tibia to accommodate a spacer used with a tibial component of a knee prosthesis.

2. Background Information

Total knee joint replacement surgery involves replacing the natural articulating surfaces of the femur and tibia with prosthetic components formed of biocompatible materials providing artificial articulating surfaces. The femoral component is often formed of a biocompatible metal such as titanium or a titanium alloy, or a cobalt-chrome alloy, with an articulating surface that is highly polished. The tibial component is often formed of a biocompatible metal baseplate and a smooth articulating surface attached to the metal baseplate that is formed of a material such as ultra-high molecular weight polyethylene that provides low friction and a low wear rate in combination with the metal articulating surface of the femoral component.

Each of the femoral and tibial components include, in addition to the mutually articulating surfaces, respective femur and tibia bone engaging surfaces. The bone engaging surfaces are often planar, or combinations of planar surfaces, and it is therefore necessary to resect the distal end of the femur and the proximal end of the tibia to provide complementary shaped planar bone surfaces for close fitting engagement with the planar bone engaging surfaces of the prosthetic components. In the case of the tibia, it is generally sufficient to provide a single, generally horizontal planar osteotomy of the proximal tibia to form a planar surface that mates with and engages a single planar inferior surface of the tibial base plate. In some cases, however, bony defects of the proximal tibia affect one of the lateral and medial condyles to a greater depth than the other. While it would be possible to perform a single planar osteotomy of the proximal tibia at a depth sufficient to resect the greater bony defect, this has the effect of resecting more bone than is desirable from the less affected side. It is therefore preferable to perform an initial planar osteotomy of the minimum depth necessary to resect the less affected side of the proximal tibia to provide good seating of the tibial base plate. A second generally horizontal osteotomy of the more affected side can be performed to resect that side of the proximal tibia to a greater depth to remove the bony defect. A spacer can then be inserted between the inferior surface of the tibial base plate and the deeper planar bone surface. A vertical sagittal osteotomy intersecting the first and second planar osteotomies will also be necessary to completely resect the bone on the more affected side.

Because of the desirability of providing good prosthesis-to-bone contact, it is necessary that the osteotomies referred to above be performed with relative precision. The vertical sagittal osteotomy should be located accurately in the medial-lateral direction to ensure alignment and close spacing between the inner edge of the tibial spacer and the vertical bone surface. The two horizontal planar osteotomies of the proximal tibia should lie in planes that are parallel to one another or otherwise conform to the relationship between the upper and lower surfaces of the spacer. In addition, the vertical spacing between the horizontal osteotomy planes should accurately conform to the thickness of the spacer. While the surgeon will have some latitude during surgery to select the thickness of the spacer to be used to correct for the bony defect that is being resected, for reasons of practicality the spacers will usually be available in only a few standard thicknesses. It would therefore be desirable to provide a tibial spacer saw guide that can accurately guide the saw blade during resection of the proximal tibia to ensure a good fit of the spacer.

One example of a tibial prosthesis with which the present invention can be used advantageously is the prosthesis described in U.S. Pat. No. 4,963,152, issued Oct. 16, 1990, and assigned to Intermedics Orthopedics, Inc.

SUMMARY OF THE INVENTION

According to one aspect of the present invention, a saw guide is provided for guiding a saw blade for resecting a medial or lateral bony defect of an initially resected tibial plateau to accommodate a spacer to be implanted beneath the inferior surface of a tibial base plate. The tibial base plate has a first pair of medial pegs and a second pair of lateral pegs adapted to be received in corresponding pairs of medial and lateral peg holes drilled in the initially resected tibial plateau. The saw guide includes a plate having an inferior surface for engaging the initially resected tibial plateau in first and second orientations. The plate includes a first pair of locating holes for receiving pins therethrough spaced and arranged to align with the pair of medial peg holes in the medial side of the initially resected tibial plateau when the plate is in the first orientation, and a second pair of locating holes for receiving pins therethrough spaced and arranged to align with the pair of lateral peg holes in the lateral side of the initially resected tibial plateau when the plate is in the second orientation. The plate further includes a lateral guide edge for guiding a saw blade for making a sagittal osteotomy when the plate is in the first orientation, the lateral guide edge being spaced and oriented relative to the first pair of locating holes. The plate further includes a medial guide edge for guiding a saw blade for making a sagittal osteotomy when the plate is in the second orientation, the medial guide edge being spaced and oriented relative to the second pair of locating holes. A block is attached to the plate anteriorly of the tibial plateau and extends generally in the medial-lateral direction, the block including at least one saw guide surface for guiding a saw blade for making a generally horizontal osteotomy of one of the medial or lateral sides of the tibial plateau, the saw guide surface being displaced from the inferior surface of the plate a distance substantially equal to the thickness of the spacer to be accommodated. The peg holes drilled in the initially resected tibial plateau serve as a reference for locating the sagittal osteotomy, and the initially resected surface of the tibial plateau serves as a reference for locating the generally horizontal resection to accommodate the spacer, thereby assuring accurate fit of a spacer which is dimensioned relative to the pegs and undersurface of the tibial base plate.

It is an object of the present invention to provide an instrument for accurately guiding a saw blade to perform osteotomies of the proximal tibia to resect bony defects to accomodate a spacer to be received inferiorly of a tibial prosthesis. Other objects and advantages of the present invention will be apparent from the following descriptions of a preferred embodiment with reference to the drawings.

DESCRIPTION OF THE PREFERRED EMBODIMENT

Figure 1:
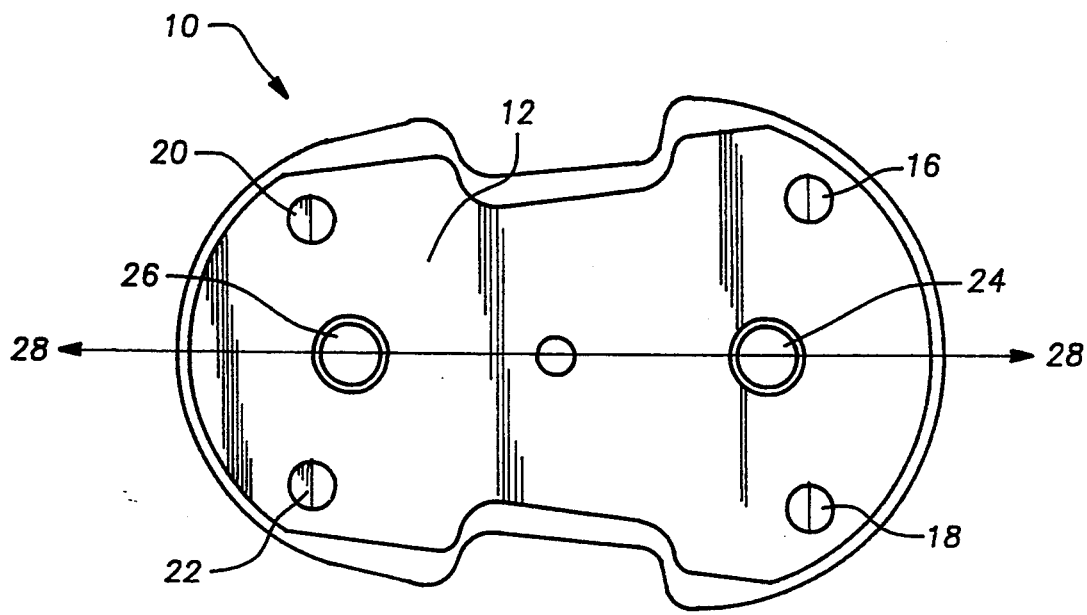
FIG. 1 is a plan view of a prior art tibial baseplate that is useful in connection with the present invention.
Figure 2:
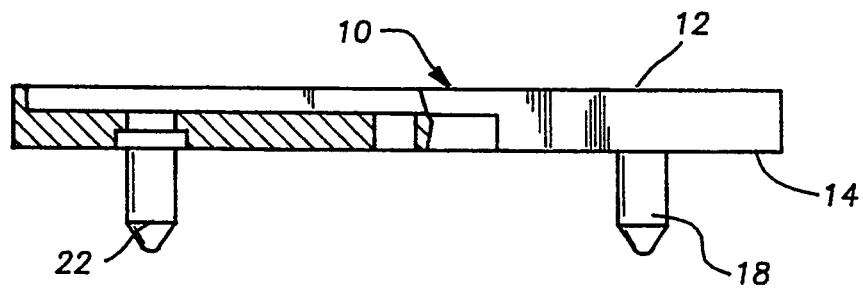
FIG. 2 is an elevational view of the prior art tibial baseplate of FIG. 1, shown partially in section.

Referring to FIGS. 1 and 2, there is shown a prior art tibial baseplate 10 comprising the metal portion of a two-piece asymmetric prosthetic tibial component, wherein the second portion (not shown) comprises a plastic tibial insert that engages the superior surface 12 of baseplate 10 and provides a bearing surface for articulation with a femoral component. Tibial baseplate 10 is designed to approximate the natural anatomic shape of the tibial plateau. Projecting perpendicularly from the inferior surface 14 are four cylindrical pegs, including medial-posterior peg 16, medial-anterior peg 18, lateral-posterior peg 20, and lateral-anterior peg 22. Between the pair of medial pegs 16, 18 and the pair of lateral pegs 20, 22, are two countersunk holes 24 and 26 on the anterior-posterior centerline 28, which accept fully-threaded cancellous bone screws (not shown). Tibial baseplate 10 is described further in U.S. Pat. No. 4,963,152, which description is hereby incorporated by reference.

Figure 3:
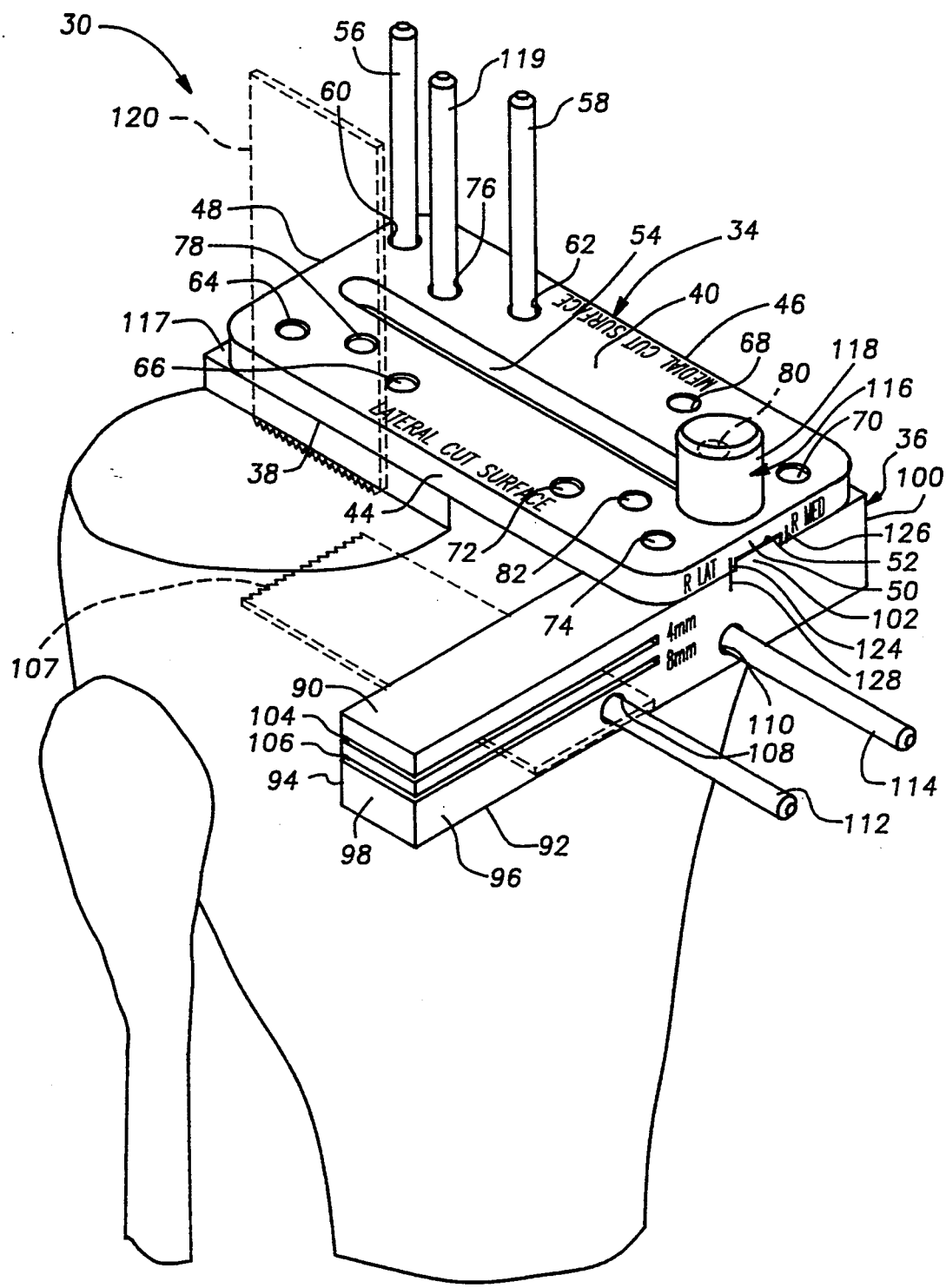
FIG. 3 is a perspective view of the present invention shown in use relative to the tibia.
Figure 4:
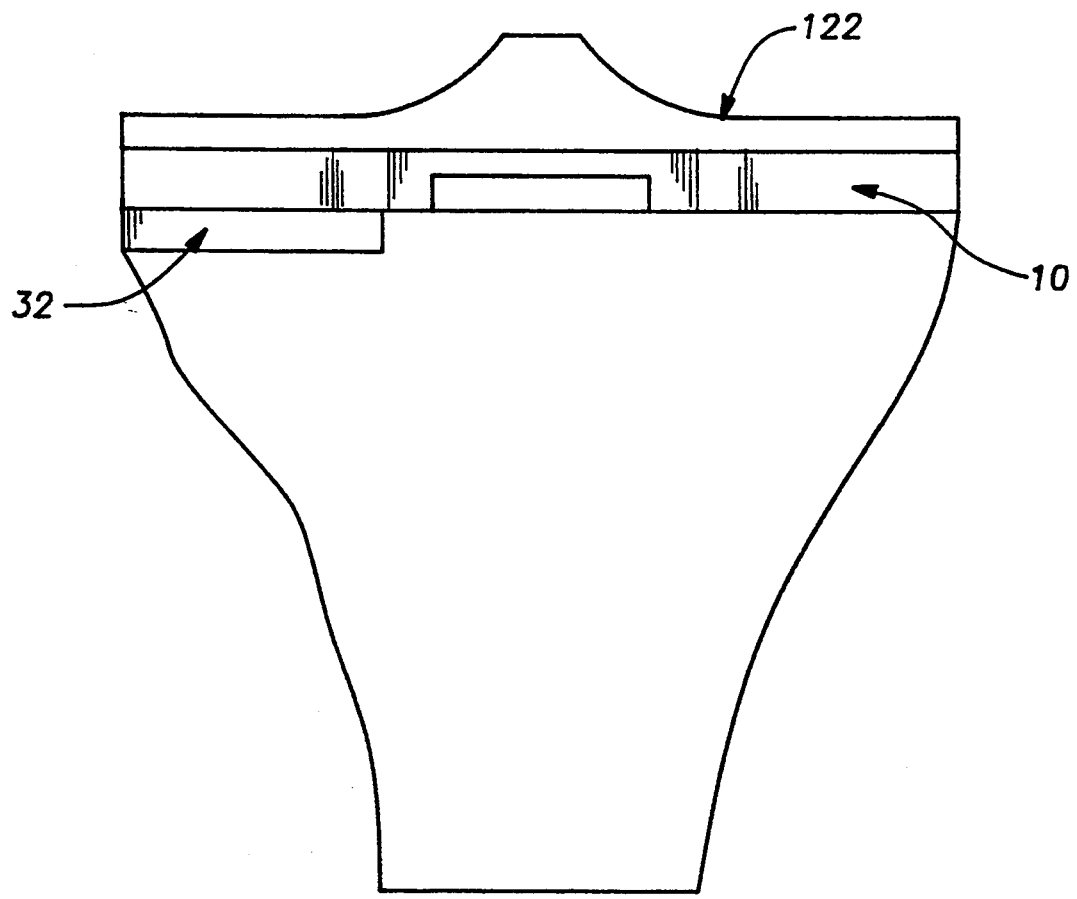
FIG. 4 is an elevational view of a proximal tibia showing an implanted tibial prosthesis and spacer.

Referring to FIG. 3, there is illustrated tibial spacer saw guide 30 which is useful for preparing the tibial plateau to receive a tibial baseplate of the general type shown in FIGS. 1 and 2, i.e., a tibial baseplate having a pair of medial pegs and a pair of lateral pegs extending from the inferior surface. More particularly, saw guide 30 is useful for resecting a bony defect of the medial or lateral condyle of the tibia to receive a spacer 32 to be placed beneath the inferior surface of the tibial baseplate 10, as shown in FIG. 4. Spacer 32 includes a pair of holes therethrough through which the corresponding pair of medial or lateral pegs of tibial baseplate 10 are received. Thus, spacer 32 is located relative to the pegs of the tibial baseplate.

Tibial spacer saw guide 30 includes two principal components, plate 34 and block 36.

Plate 34 is a generally rectangular flat plate having a substantially planar inferior surface 38 and a substantially planar superior surface 40. Plate 34 is bounded by a lateral guide edge 44, a medial guide edge 46, and end edges 48 and 50. A longitudinal rectangular groove 52 in inferior surface 38 of plate 34 extends the length of plate 34 and is open at end edges 48 and 50. A longitudinal slot 54 extends substantially the length of plate 34 and is aligned with groove 52. Slot 54 extends through plate 34 from superior surface 40 to the bottom wall of groove 52. In each corner of plate 34, there is situated a pair of locating holes for receiving therethrough locating pins 56 and 56. Right medial locating holes 60 and 62 are situated proximate the corner defined by end edge 48 and medial guide edge 46. Right lateral locating holes 64 and 66 are situated proximate the corner defined by end edge 48 and lateral guide edge 44. Left medial locating holes 68 and 70 are situated proximate the corner defined by end edge 50 and medial guide edge 46. Left lateral locating holes 72 and 74 are situated proximate the corner defined by end edge 50 and lateral guide surface 44. Associated with each pair of medial or lateral locating holes is a third stabilizing hole situated on the same side of groove 52. Stabilizing hole 76 is associated with locating holes 60 and 62. Stabilizing hole 78 is associated with locating holes 64 and 66. Stabilizing hole 80 is associated with locating holes 68 and 70. Stabilizing hole 82 is associated with locating holes 72 and 74. Block 36 is a generally elongated rectangular block having a planar superior surface 90, inferior surface 92, sides 94 and 96,7 and ends 98 and 100. A rectangular tongue 102 extends from superior surface 90 transversely to block 36 proximate end 100. Tongue 102 is sized and dimensioned to be received in groove 52 of plate 34 in a close-fitting but slidable relationship. Planar superior surface 90 of block 36 engages planar inferior surface 38 of plate 34 such that block 36 is maintained substantially parallel to plate 34. Tongue 102 interacts with groove 52 to maintain the longitudinal axis of block 36 substantially perpendicular to the longitudinal axis of plate 34. Saw guide slots 104 and 106 extend through block 36 from side 94 to side 96, and extend to end 98. Slot 104 is parallel to superior surface 90 and displaced 4 mm therebelow. Slot 106 is also parallel to superior surface 90 but is displaced 8 mm therebelow. Each of slots 104 and 106 are sized to received therethrough a saw blade 107 such that the saw blade can reciprocate in the lateral-medial direction and can be displaced in the anterior-posterior direction, but is restrained from motion in the vertical direction. A pair of stabilizing holes 108 and 110 extend through block 36 from side 94 to side 96 and are provided to optionally receive stabilizing pins 112 and 114 therethrough.

A thumbscrew 116 having a knurled knob 118 includes a threaded shaft that extends through longitudinal slot 54 of plate 34 and is received in a correspondingly threaded bore in the superior surface of tongue 102 of block 36. When thumbscrew 116 is tightened, the superior surface 90 of block 36 is drawn into tight engagement with the inferior surface 38 of plate 34 to prevent relative movement between plate 34 and block 36. When thumbscrew 116 is loosened slightly, block 36 can be slid from one end of plate 34 to the other, with tongue 102 sliding in groove 54. When thumbscrew 116 is loosened to a greater extent, block 36 can be rotated 180° about the axis of thumbscrew 116 and positioned to extend in the opposite direction from that illustrated. Thus, it will be understood that block 36 can be oriented in any one of four possible orientations relative to plate 34. In addition, within any one general orientation, some repositioning in the anterior-posterior direction is permitted by loosening thumbscrew 116.

Referring in particular to FIG. 3, use of tibial spacer saw guide 30 cain be described as follows. Using a tibial cutting guide as generally understood in the prior art, an initial osteotomy of the proximal tibia is performed to resect the least involved condyle of the tibial plateau to leave a flat proximal bone surface 117. It should be understood that the initial osteotomy is generally similar to the osteotomy that would be performed in the prior art technique, except that the initial osteotomy will not completely resect the bony defect of the most affected side because the natural tibial plateau on the most affected side will be below the level of the initial osteotomy. After checking the initially cut surface 117 for flatness, a proximal tibial drill guide as known in the prior art is selected from among several sizes available, and the best fitting drill guide is positioned onto the initially cut surface of the proximal tibia. The drill guide has six holes corresponding in location to pegs 16, 18, 20 and 22, and screw holes 24 and 26, of a correspondingly sized tibial baseplate 10 of FIG. 1. Holes are drilled in the tibial plateau at the site of each of the drill guide holes. So far the procedure has been similar to the prior art technique note: involving spacers and has not yet utilized the apparatus of the present invention.

At this point, the present invention comes into use. For the purposes of the present description, it should be assumed that the greater bony defect involves the lateral condyle of the right tibia, and use of saw guide 30 will be described with that assumption, as illustrated in FIG. 3. The drill guide is removed and the pair of medial holes corresponding in location to pegs 16 and 18 of tibial baseplate 10, in the non-defective side of the initially resected surface, are filled with smooth guide pins 56 and 56. The associated hole on the medial side of the resected tibial surface corresponding to screw hole 24 of tibial baseplate 10 is filled with a stabilizing pin 119.

Block 36 is assembled to plate 34 proximate end 50 so as to extend laterally in the medial-lateral direction. Plate 34 is placed over pins 56, 58 and 119 such that the pins pass through holes 60, 62 and 76, respectively, and plate 34 is lowered until inferior surface 38 rests flush against initially resected surface 117 of the proximal tibia. When so placed, block 36 is disposed anteriorly of the tibia. One or more pins 112 and 114 can optionally be inserted through holes 108 and 110 in block 36 and driven into the anterior surface of the tibia to provide additional fixation and stability of saw guide 30 relative to the proximal tibia. A vertical sagittal osteotomy is made using, for example, a one inch wide saw blade 120 held flush against lateral guide edge 44. The vertical osteotomy is made approximately 4 mm or 8 7216 mm deep, depending on the size of the defect and the size of the spacer that has been selected. Preferably, following completion of the vertical osteotomy, a free saw blade is left imbedded in the bone to act as a protector to avoid undercutting the non-involved tibial plateau surface when the horizontal osteotomy is performed. As used herein, the term "horizontal osteotomy" refers to an osteotomy that is generally transverse to the longitudinal axis of the tibia assuming that the longitudinal axis of the tibia is oriented vertically. The term "horizontal" includes not only orientations substantially perpendicular to the longitudinal axis of the tibia, but also orientations deviating from true horizonal at angles up to about 45°. A horizontal osteotomy is made using a similar saw blade 107 inserted through either slot 104 or 106, depending on the size of the defect and the size of the spacer that has been selected. The saw blade is moved in the anterior-posterior direction and in the medial-lateral direction until the affected side has been completely resected, as shown in FIG. 3. Saw guide 30 and pins 56, 58 and 119, and pins 112 and 114, if used, are then removed from the tibia.

Following testing with a trial spacer and trial tibial base plate, and trial femoral component, the spacer 32 (FIG. 4) is secured to the inferior surface of the prosthetic tibial base plate using bone cement or other securing means as may be desired, and the composite base plate and spacer are placed on the prepared surface of the tibia and secured in place with a pair of cancellous bone screws received through screw holes 24 and 26 of tibial baseplate 10. An appropriately sized polyethylene tibial insert 122 (FIG. 4) is placed on the superior surface 12 of tibial baseplate 10, followed by implantation of the femoral component on the appropriately prepared distal femur.

It should be understood that the above-described procedure could also be performed to resect the medial condyle of the right tibia, or the medial or lateral condyle of the left tibia, using the same saw guide 30. For instance, by reversing the orientation of block 36 so that end 98 extends medially in the medial-lateral direction, and by using locating holes 64, 66 and 78 of plate 34 to fix plate 34 to the lateral side of the tibial plateau, the medial side of the right tibia could be resected to accommodate a spacer. In addition, by moving block 36 proximate end 48 of plate 34 and rotating plate 34 so that block 36 is disposed anteriorly of the tibia, saw guide 30 can be used on the left tibia. To assist the physician in orienting block 36 properly relative to plate 34, saw guide 30 is provided with alignment indicia. For example, end edge 50 is provided with a pair of scribe marks 124 and 126 disposed on opposite sides of groove 52 and labeled "R LAT" and "R MED", respectively. Another scribe mark 128 on side 96 of block 36 aligns with scribe mark 124 when block 36 and plate 34 are oriented as shown in FIG. 3. This indicates that saw guide 30 is set up for guiding an osteotomy of the right lateral proximal tibia. The vertical sagittal osteotomy is guided by lateral guide edge 44 labeled "LATERAL CUT SURFACE." Another scribe mark (not shown) corresponding to scribe mark 128 is located on side 94 of block 36 and aligns with scribe mark 126 when saw guide 30 is set up for guiding an osteotomy of the right medial proximal tibia. In that case, the vertical sagittal osteotomy is guided by guide edge 46 labeled "MEDIAL CUT SURFACE." In analogous fashion, scribe marks corresponding to scribe marks 124 and 126 are disposed on end edge 48 of plate 34, but are labeled "L LAT" and "L MED." It should be understood that regardless of which tibia is involved, lateral guide edge 44 will always be used for the sagittal osteotomy for a lateral spacer, and medial guide edge 46 will always be used for the sagittal osteotomy for a medial spacer. It should further be understood that the vertical sagittal cut is located particularly accurately because the lateral guide edge is positioned relative to the locating holes, which in turn correspond to the location of the pegs on the inferior surface of the tibial baseplate. Thus, insofar as the spacers themselves are dimensioned relative to the tibial baseplate pegs, the medial-lateral fit between the spacer and resected bone is quite good. Similarly, the horizontal osteotomy guide slots are located relative to the inferior surface of the plate 34, which corresponds to the inferior surface of the tibial baseplate. Thus, insofar as the spacers themselves are dimensioned relative to the inferior surface of the tibial baseplate, the superior-inferior fit between the spacer and resected bone is likewise quite good.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims. For example, while slots 104 and 106 of block 36 of the preferred embodiment are illustrated as being substantially parallel to inferior surface 38 of plate 34, it should be understood that slots 104 and 106 can be disposed at an acute angle up to about 45° sloping downwardly and away from the plane of plate 34 in the medial-lateral direction. Such an orientation would allow a horizontal osteotomy to be performed to accommodate a wedge-shaped spacer.

We claim:

1. A saw guide for guiding at least one saw blade for resecting a bony defect of a medial or lateral side of a proximal end of a tibia, said proximal end having a resected planar proximal end surface oriented substantially perpendicular to said tibia, a first pair of drill holes oriented substantially parallel to said tibia and located on the medial side of said proximal end, and a second pair of drill holes oriented substantially parallel to said tibia and located on the lateral side of said proximal end, to accomodate a spacer to be implanted between an inferior surface of a tibial baseplate prosthesis and said proximal end, said tibial baseplate prosthesis having first and second pairs of pegs extending from said inferior surface adapted to be received in said first and second pairs of drill holes, respectively, said saw guide comprising:

a plate, said plate including means for engaging said planar proximal end surface in alternate first and second positions, first alignment means for aligning said plate with said first pair of drill holes, and second alignment means for aligning said plate with said second pair of drill holes, wherein when said means for engaging engages said planar proximal end surface in said first position, said first alignment means is aligned with said first pair of drill holes and when said means for engaging engages said planar proximal end surface in said second position, said second alignment means is aligned with said second pair of drill holes, first saw guide means spaced and oriented relative to said first alignment means for guiding said at least one saw blade for making a sagittal osteotomy of said proximal end when said means for engaging engages said planar proximal end surface in said first position, and second saw guide means spaced and oriented relative to said second alignment means for guiding said at least one saw blade for making a sagittal osteotomy of said proximal end when said means for engaging engages said planar proximal end surface in said second position; and a block attached to said plate, said block being disposed anteriorly of said tibia when said means for engagement engages said planar proximal end surface, said block including third saw guide means for guiding said at least one saw blade for making a generally horizontal osteotomy of one of said medial and lateral sides of said proximal tibia, said third saw guide means being displaced from said means for engaging in a direction parallel to said tibia a distance substantially equal to a thickness of the spacer to be accomodated;

whereby said first and second pairs of drill holes in the proximal tibia serve as references for locating the sagittal osteotomy, and whereby the resected planar proximal end surface of the tibia serves as a reference for locating the generally horizontal osteotomy.

2. The saw guide of claim 1, in which said first alignment means of said plate is proximate said second saw guide means and said second alignment means of said plate is proximate said first saw guide means.

3. The saw guide of claim 2, in which said third saw guide means of said block is defined by a slot through said block.

4. The saw guide of claim 2, in which said block has a superior surface in engagement with said inferior surface of said plate.

5. The saw guide of claim 1, in which said third saw guide means of said block is defined by a slot through said block.

6. The saw guide of claim 1, in which said block has a superior surface in engagement with said inferior surface of said plate.

7. The saw guide of claim 6, in which said block is reorientable in first and second orientations relative to said plate, said third saw guide means of said block being positioned laterally of said first saw guide means of said plate when said block is in said first orientation, and said third saw guide means of said block being positioned medially of said second saw guide means of said plate when said block is in said second orientation.

8. The saw guide of claim 1, in which said block is reorientable in first and second orientations relative to said plate, said third saw guide means of said block being positioned laterally of said first saw guide means of said plate when said block is in said first orientation, and said third saw guide means of said block being positioned medially of said second saw guide means of said plate when said block is in said second orientation.

9. The saw guide of claim 8, in which said plate includes first and second end edges at opposite ends of said plate, each of said first and second end edges connecting said first and second saw guide means, said block being repositionable in first and second positions relative to said plate, said block being proximate said first end edge in said first position, and said block being proximate said second end edge in said second position.

10. The saw guide of claim 1, in which said plate includes first and second end edges at opposite ends of said plate, each of said first and second end edges connecting said first and second saw guide means, said block being repositionable in first and second positions relative to said plate, said block being proximate said first end edge in said first position, and said block being proximate said second end edge in said second position.

11. The saw guide of claim 10, in which said plate includes a longitudinal slot therethrough extending from proximate said first end edge to proximate said second end edge through which is received in siding relationship a thumbscrew that is threadedly connected to said block such that said block is drawn tight against said plate and secured against movement relative thereto when said thumbscrew is tightened, and such that said block is free to move between said first position proximate said first end edge and said second position proximate said second end edge when said thumbscrew is loosened.

12. The saw guide of claim 1, in which said plate includes a longitudinal groove in the inferior surface thereof, and in which said block is elongated and has a longitudinal axis, said block including a tongue oriented perpendicular to the longitudinal axis of said block and received in sliding relationship within the longitudinal groove of said plate to maintain the longitudinal axis of said block substantially perpendicular to the longitudinal axis of said plate.

* * * * *